United States Patent
Sentmanat (10) Patent No.: US 6,578,413 B2
(45) Date of Patent: Jun. 17, 2003

(54) DUAL WINDUP EXTENSIONAL RHEOMETER

(75) Inventor: Martin Lamar Sentmanat, Akron, OH (US)

(73) Assignee: The Goodyear Tire & Rubber Company, Akron, OH (US)

( * ) Notice: Subject to any disclaimer, the term of this patent is extended or adjusted under 35 U.S.C. 154(b) by 0 days.

(21) Appl. No.: 09/849,934

(22) Filed: May 4, 2001

(65) Prior Publication Data

US 2001/0049972 A1 Dec. 13, 2001

Related U.S. Application Data (63) Continuation of application No. PCT/US98/24003, filed on Nov. 11, 1998.

(51) Int. Cl.[7] .................................................. G01L 5/04
(52) U.S. Cl. ........................................................ 73/160
(58) Field of Search ............................... 73/261, 861.78, 73/861.77, 861.02, 861.03, 160, 159, 158; 418/206; 254/175.5; 242/433.3, 433.2, 473.4, 45; 187/20; 140/119

(56) References Cited

U.S. PATENT DOCUMENTS

| | | | |
|---|---|---|---|
| 3,640,127 A | | 2/1972 | Meissner |
| 3,693,425 A | | 9/1972 | Starita et al. |
| 3,776,519 A | * | 12/1973 | Hamilton .................... 242/362 |
| 4,295,369 A | * | 10/1981 | Wendelboe .................... 73/261 |
| 5,447,062 A | * | 9/1995 | Kopl et al. .................... 73/261 |
| 5,704,767 A | * | 1/1998 | Johnson ........................ 417/43 |

FOREIGN PATENT DOCUMENTS

| | | |
|---|---|---|
| DE | 2138504 | 2/1973 |
| DE | 2243816 | 3/1974 |
| GB | 1287367 | 8/1972 |
| JP | 5512436 | 11/1980 |

OTHER PUBLICATIONS

Connelly, R.W., Garfield, L.J. and Pearson, G.H. "Local Stretch History of a Fixed–End Constant–Length–Polymer–Melt Stretching Experiment Journal of Rheology", 23(5), 651–662 (1979).

Wassner, E. "Determination of True Extensional Viscosities with a Meissner–type Rheometer (RME)" BASF Aktiengesellschaft.

Meissner, J. and Hostettler, J. "A New Elongational Rheometer for Polymer Melts andOther Highly Viscoelastic Liquids"Rheologica Acta 33 pp.1–21 (1994).

Meissner, J. "Development of a Universal Extensional Rheometer for the Uniaxial Extension of Polymer Melts" Transaction of the Society of Rheology 16:3, pp.405–420 (1972).

Meissner,J., Raible, T. and Stephenson, S.E. "Rotary Clamp in Uniaxial and Biaxial Extensional Rheometru of Polymer Melts" Journal of Rheology 25(1) pp. 1–28 (1981).

Meissner, J. "Polymer Melt Elongation—Methods,Results and Recent Developments" Polymer Engineering and Science 27:8 pp. 537–546 (Apr. 1987).

Sebtmanat, Martin L. "A Novel Extensional Rheometer for Elastomers" presented at 2001 GRC: Elastomers, Networks and Gels (Aug. 2001).

Kukwenko, V.S., Sultanov, U., Abdumanonov, A., Shamsidinov, M.I. and Karimov, S.N. Strength and Operating Lifetime Optical Fibers: Technical Physics Letters 19(1) pp. 58–59 (Jan. 1993).

* cited by examiner

Primary Examiner—Hezron Williams
Assistant Examiner—Jewel V. Thompson
(74) Attorney, Agent, or Firm—Howard M. Cahn (57) ABSTRACT

An extensional rheometer comprises a drive shaft connected to an armature, wherein the armature is further connected to a torque shaft, and two rotatable drums are mounted in the armature. One end of a sample is connected to each drum, and the drums are rotated, stretching the sample until the sample breaks. The torque in the apparatus caused by the stretching of the sample is measured. Environmental control may be provided for testing samples under different conditions.

20 Claims, 6 Drawing Sheets

DUAL WINDUP EXTENSIONAL RHEOMETER

This is a Continuation of international application number PCT/US98/24003, filed on Nov. 11, 1998, presently pending.

TECHNICAL FIELD

The invention relates to a rheometer or rheometer attachment which is used to measure the viscosity and stress relaxation of polymers, elastomers, and rubber compounds in simple extension.

BACKGROUND ART

Joachim Meissner, in the review article "Polymer Melt Elongation-Methods, Results, and Recent Developments" in Polymer Engineering and Science, April 1987, Vol. 27, No. 8, pp. 537–546 describes different extensional rheometers that have been developed in the prior art. Meissner is also the author of several patents on the subject including U.S. Pat. No. 3,640,127, dated Feb. 8, 1972, German 2138504, dated Aug. 2, 1971, German 2243816, dated Sep. 7, 1972 and U.K. 1287367.

Extensional rheometer designs by Cogswell, Vinogradov, and later Münstedt had in common that one end of the polymer fiber or filament that was used for testing was fixed to a load cell/indicator, while the other end was stretched by mechanical means to a finite maximum elongation. Accordingly, these rheometers operated with a non-uniform extensional rate throughout the sample particularly near the clamped ends of the fiber. Meissner overcame these difficulties with his dual rotary clamp design in which rotary clamps stretched the fiber at either end over a fixed gauged length. See, for example, "Rotary Clamp and Uniaxial and Biaxial Extensional Rheometry of Polymer Melts" by J. Meissner, et al., Journal of Rheology, Vol. 25, pp. 1–28 (1981) and "Development of a Universal Extensional Rheometer for the Uniaxial Extension of Polymer Melts", by J Meissner, Transactions of the Society of Rheology, Vol. 16, No. 3, pp. 405–420 (1972). In a further development of this type of rheometer, in order to improve the transfer of the circumferential speed of the clamps to the local speed of the sample at the location of clamping (strain rate lag), two rotary clamps in the prior art devices were replaced by Meissner and Hostettler as illustrated in "A New Elongational Rheometer for Polymer Melts and other Highly Viscoelastic Liquids", Rheological Acta, Vol. 33, pp. 1–21 (1994) with matched/grooved, metal conveyor belts. With this design, however, a measurement was limited to a single rotation of the clamps corresponding to a Hencky strain of seven, and the maximum extensional rate was limited to 1/s (a reciprocal second). The extensional viscosity was determined from the force required to deform the fiber, which was measured by the deflection of leaf springs supporting one set of rotating clamps.

Other techniques used to measure extensional viscosity involved winding one end of a fiber around a drum and measuring the resultant stretching force at the other fixed end of the fiber, as illustrated in U.S. Pat. No. 3,693,425 (1972) by J M Starita et al. Like the earlier designs, this method imparted a non-uniform extensional deformation to the free gauge length of the stretched fiber, particularly at the fixed end of the fiber. Further, the windup was uncontrolled and precautions had to be taken to ensure that windup did not take place over a portion of previously wound fiber.

DISCLOSURE OF THE INVENTION

An apparatus for measuring the rate of extensional flow of low modulus solids comprises; (a) a drive shaft mounted in an armature, the armature being connected to a torque shaft, and (b) two rotatable drums in proximity to one another, wherein a first drum is mounted in the armature substantially in alignment with the torque and drive shafts, and a second drum is adjacent thereto.

In the illustrated embodiment, the first and second drums are in substantially parallel alignment, are mounted on bearings, and may have associated therewith means for directing the windup of a sample on the drums. The drums may be geared to be counter rotating or co-rotating. In the illustrated embodiment, the drums are geared such that the drums rotate at the same speed.

Also provided is a method for measuring the rate of flow of low modulus solids comprising the steps of, a) providing an apparatus for measuring the rate of extensional flow of low modulus solids comprising a drive shaft mounted in an armature wherein the armature is further connected to a torque shaft, two rotatable drums in proximity to one another wherein the first drum is mounted in the armature substantially in alignment with the torque and drive shafts and the second drum is adjacent thereto), b) fixing a sample to both drums, one end of said sample being attached to each drum, c) causing the two ends of the sample to be pulled away from each other by rotation of the drums, and d) measuring the torque created in the torque shaft by the drawing of the sample.

The method may further comprise the steps of measuring the maximum torque achieved by the sample and measuring the lapsed time from the start of the measurement to the breaking of the sample. In the illustrated embodiment of the method, the two rotatable drums are mounted substantially in parallel alignment on bearings, and the drums have associated therewith means for directing the windup of a sample on the drums.

The dual windup threaded drum extensional rheometer illustrated, makes possible the windup of each end of a fiber and imparts a uniform extensional deformation to the unsupported pre gauge length of the fiber, and allows for large extensional deformations by allowing multiple drum rotations with a threaded drum design.

The rheometer provides a simple design and method to measure the extensional flow properties of polymers, elastomers and compounds. The rheometer of the invention can be attached to any commercially available rotational rheometer, and can be made small enough to fit within the environmental chamber of a rotational rheometer in order to measure extensional flow properties as a function of temperature. The invention may also be part of, or be incorporated into a new type of rheometer. The apparatus can also be used to measure the extensional properties of viscoelastic solids.

BRIEF DESCRIPTION OF DRAWINGS

FIG. 5, FIG. 6 and FIG. 6A illustrate the apparatus of the invention contained in an environmental chamber, wherein FIG. 6A illustrates a top of view of an alternative embodiment of the apparatus where the drums are co-rotating.

DETAILED DESCRIPTION OF THE INVENTION

With reference now to FIGS. 1–4, the apparatus 10 comprises a drive shaft 14, which is mounted on bearings 28 that are attached to armature 16, armature 16 further being attached to torque shaft 12. Mounted within armature 16 are primary windup drum 18 and secondary windup drum 20.

Although primary windup drum 18 and secondary windup drum 20 are illustrated as being mounted parallel to one another and directly adjacent to one another, those skilled in the art will recognize that said drums can be mounted at different angles relative to one another, and different angles relative to the torque and drive shafts. Such angular mounting may affect how calculations are done in determining results, but would not affect the results achieved by the apparatus.

In the illustrated embodiment, primary windup drum 18 is illustrated as being in direct alignment with drive shaft 14 and torque shaft 12. Those skilled in the art will recognize that this alignment is not necessary for operation of the apparatus, but is preferred to make construction easier and simplify the calculations of torque.

Each of the windup drums 18, 20 have associated therewith means for securing a filament to the drum as required to carry out the measurements desired. In the illustrated embodiment the securing means is filament securing clamp 22.

Windup drums 18, 20 are mounted on armature 16 through ball bearings 28 and are further connected to gears 36 and 26 respectively. Drive shaft 14 turns gear 36, gear 36 turns gear 26 which causes rotation of secondary windup drum 20. The resistance provided by the stretched sample to the turning of secondary windup drum 20 imparts a force to the intermeshing gears 36 and 26, which in turn imparts a force to armature 16. This force tends to turn the armature in a direction opposite the direction of rotation of secondary windup drum 20, wherein the tendency of the armature to turn creates a torque in torque shaft 12 that can be measured.

In the operation of the apparatus of the invention, the ends of a fiber sample are secured to the windup drums, and constant rotation of the drums imparts a constant, uniform extensional deformation rate to the unsupported pre gauge length of the fiber. The extensional deformation of the fiber offers a resistance to deformation which is related to the extensional viscosity of the sample, which in turn offers a resistance to the drum rotation in the form of a resultant torque on the torque armature. By measuring the resultant torque on the armature, the extensional viscosity of the fiber may be calculated for a given extensional deformation rate and temperature.

Figure 1:
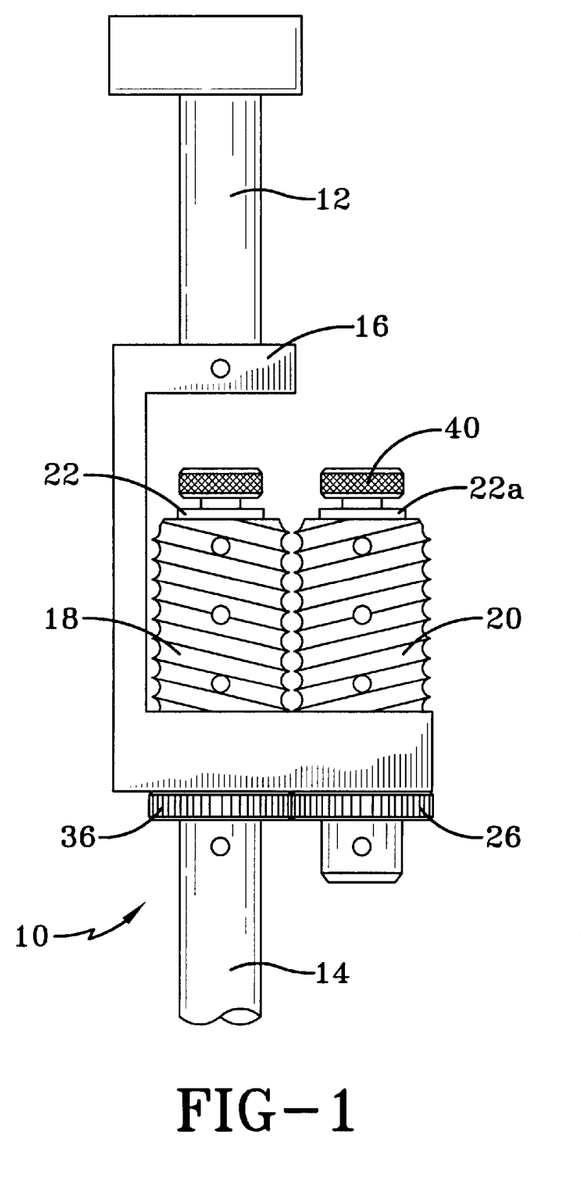
FIG. 1 illustrates a side view of the apparatus of the invention illustrating the armature and two parallel rotating drums.
Figure 2:
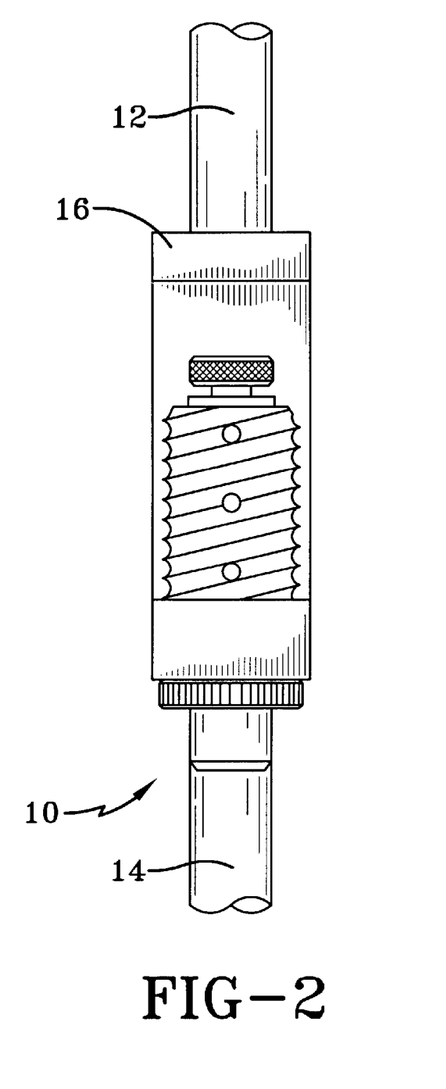
FIG. 2 illustrates the apparatus of FIG. 1 rotated 90 degrees.
Figure 3:
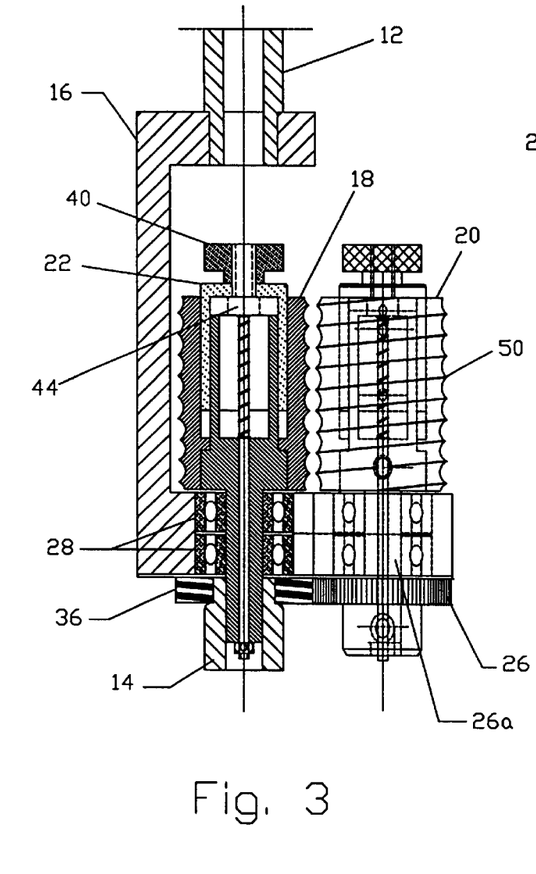
FIG. 3 illustrates an enlarged view of the armature and the rotation drums.
Figure 4:
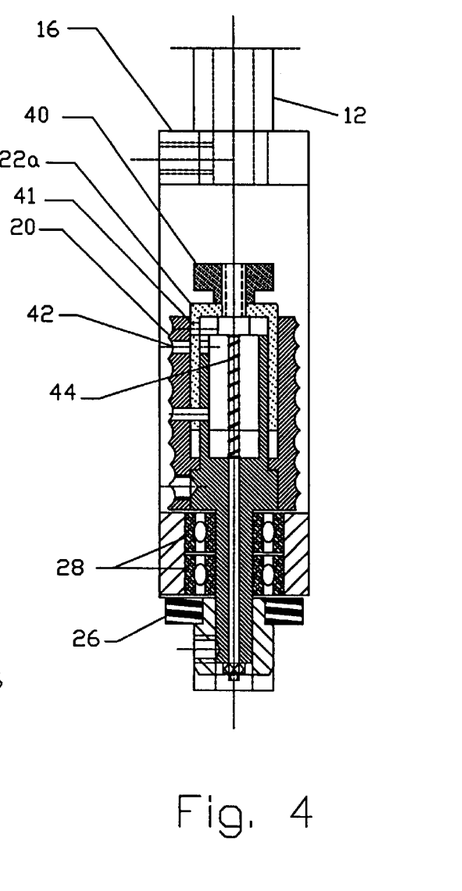
FIG. 4 illustrates the apparatus of FIG. 3 rotated 90 degrees.

With reference specifically to FIGS. 3 and 4, in an enlarged view of the apparatus, details of the construction of the apparatus can be seen. To those skilled in the mechanical art, other mechanical embodiments of the inventive concepts described herein will be readily apparent.

The same type of filament securing clamp 22 is used with both primary windup drum 18 and secondary windup drum 20. Accordingly, filament securing clamp 22 for primary windup drum 18 is illustrative for the method used to secure a filament to both drums in the illustrated embodiment. Filament securing clamp 22 has associated therewith a filament securing clamp knob 40 which is used by the operator to secure a filament 34 or 34A (see FIGS. 5 and 6A) to a windup drum 18, 20. By depressing the securing clamp knob 40, the guide hole 41 in the filament securing clamp 22 aligns with the guide hole 42 of the windup drum (see FIG. 4) and the filament 34, 34A is threaded through said aligned holes 41 and 42. Releasing the clamp knob 40 relieves the securing clamp compression spring 44 causing the edge of the filament securing clamp guide hole 41 to bear against the filament 34, 34A, thus securing the filament in said windup drum guide hole 42.

Filament guide means are used to control the manner in which the filament is wound up on the drums, and in the illustrated embodiment the filament guide means is provided by the helical threading 50 on the drums. Thus, in operation, when the windup drums 18, 20 are turned, the filament is guided into the helical threads on the drums so that there is no overlap of the filament and there is no distortion in the extensional measurements.

Figure 5:
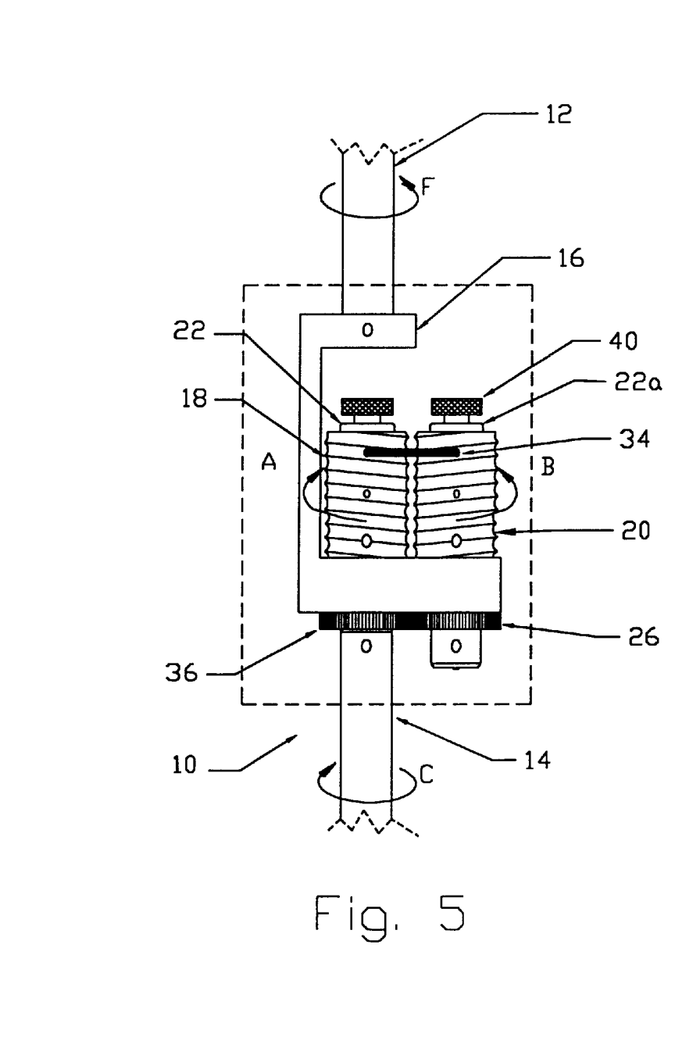
Figures 6, 6A:
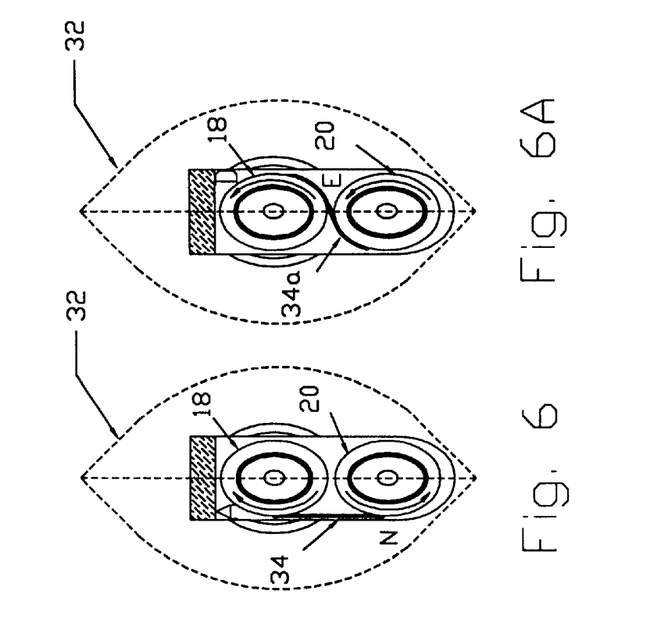

With reference now to FIGS. 5, 6 and 6A, the apparatus is illustrated as being contained within an environmental chamber 32 which can be used to heat or cool the sample as desired. In the operation of the apparatus, after a filament is secured to primary windup drum 18 and secondary windup drum 20, drive shaft 14 is rotated in the direction of arrow C, which causes primary windup drum 18 to rotate in the direction of arrow A. Since, in the embodiment illustrated in FIG. 5, gear 36 and gear 26 are intermeshing, turning of gear 36 causes secondary windup drum 20 to rotate the opposite direction, i.e., in the direction of arrow B. When filament 34 is secured to primary windup drum 18 and secondary drum 20 as illustrated in FIG. 5, the counter rotation of drums 18, 20 cause filament 34 to be stretched. As filament 34 is stretched, its resistance to the turning of drums 18 and 20 increases, wherein the resistance of the filament is transferred to secondary windup drum 20 which has a tendency to turn armature 16 in the opposite direction, thereby creating a resultant torque on torque shaft 12 in the direction of arrow F.

The apparatus is designed so that torque shaft 12 does not actually move, but a torque on torque shaft 12 activates a force rebalance transducer which, through a closed feedback loop in the apparatus, develops a current which tends to counteract the torque imposed on torque shaft 12 by the secondary windup drum, and the current required to counteract this torque is measured, thereby measuring the torque created. Such force rebalance transducers are well known to those skilled in the art.

Other techniques of measuring torque are known to those skilled in the art, and such other techniques can be used with the apparatus of the invention.

Environmental chamber 32 is designed to measure the rheology of samples from −70 degrees centigrade to 300 degrees centigrade. Measurements at lower temperatures are designed to measure extensional rheology as it relates to the $T_g$ (glass transition) of the sample, and the extensional flow of the materials at higher temperatures is related to the melt/viscosity of the sample. Environmental chamber 32 can be in the form of an oven or an oil bath, or any other means known to those skilled in the art for controlling the physical state of a sample.

An embodiment is illustrated in FIG. 6A wherein the primary windup drum 18 and the secondary windup drum 20 are co-rotational. Co-rotation of drums 18 and 20 can be achieved simply by adding an additional gear (not shown)

between spur gears 26 and 36. When co-rotational primary windup drums 18 and second windup drums 20 are used, the sample filament 34A will be attached to the drums as illustrated in FIG. 6A i.e., between the drums. The resultant torque in such an embodiment will be opposite the resultant torque illustrated in FIG. 5. The same principles of operation as described with respect to an apparatus with counter rotating drums apply.

With reference again to FIG. 5, a sample 34 in its original state has a relatively substantial thickness as represented by the thick line in the drawing. After the secondary and the primary windup drums have been rotated, the sample is stretched over the diameter of the drums, and accordingly, its cross-sectional thickness is substantially reduced. It is the resistance of the material to stretch, and continued stretching that creates a force on the armature, which transmits a torque to torque shaft 12.

Figure 7:
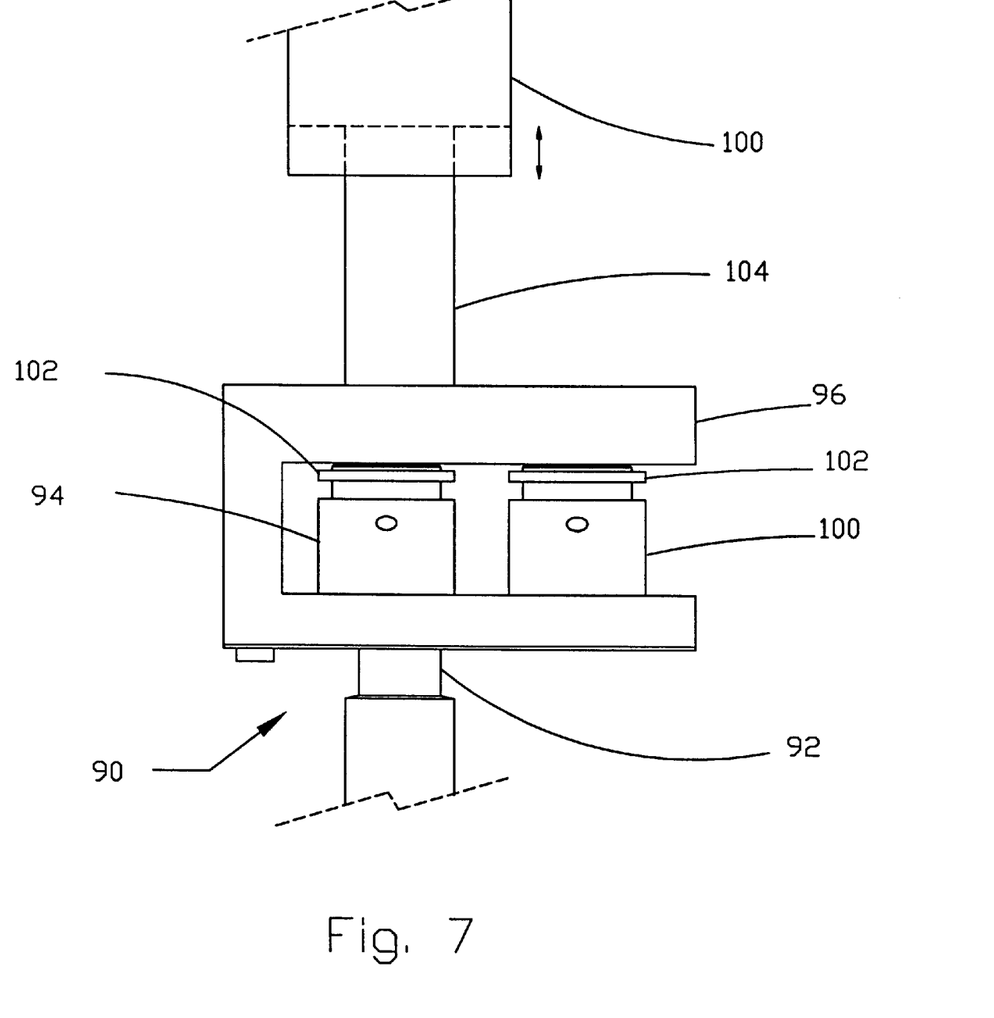
FIG. 7, FIG. 8 and FIG. 8A illustrate an alternative embodiment of the apparatus of the invention.
Figure 8:
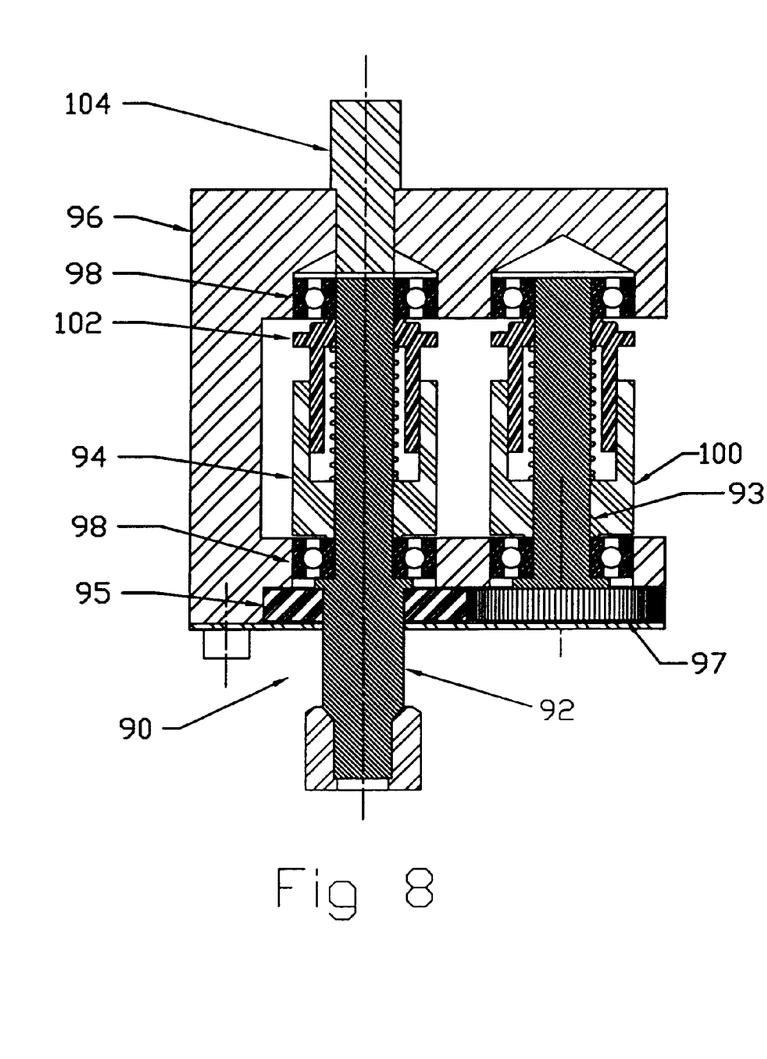
Figure 8A:
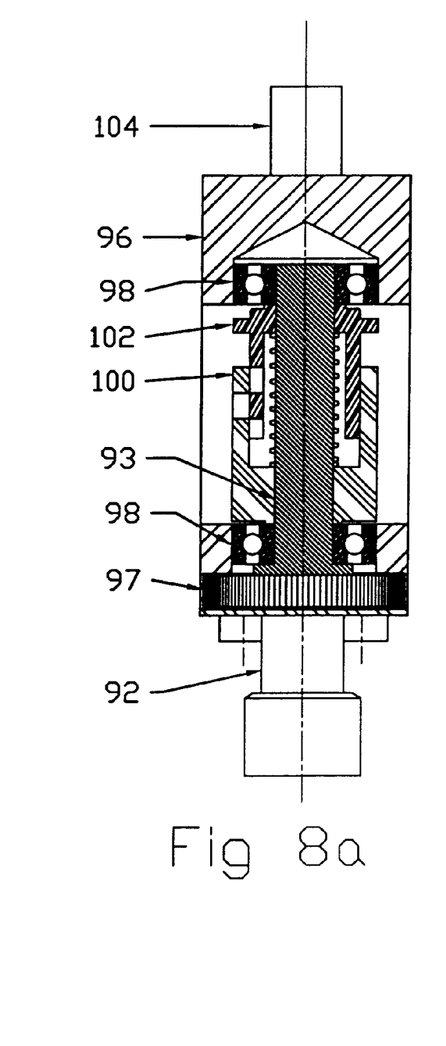

With reference now to FIGS. 7, 8, and 8A, in an alternative embodiment, primary drum 94 and secondary drum 100 of apparatus 90 of the invention can be made smooth, without sample guiding means since many samples are not long enough to survive one rotation of the drums. The securing clamp 102 of each drum can be spring-loaded and fashioned to slide up and down primary drive shaft 92 and secondary shaft 93 of the apparatus during fiber loading and unloading. Also, the torque armature 96 can be made to house intermeshing gears 95 and 97 and to support the ends of the primary and secondary shafts of the apparatus with radial ball bearings 98, rather than having the shafts cantilevered as in the embodiment earlier described.

When the invention is used as a fixture on a commercial rotational rheometer in which one of the fixture adapters is affixed to a reciprocating, movable stage, a miniature telescoping ball spline 106 can be incorporated onto the torque shaft 104. This telescoping ball spline ensures the translation of torque, but not compressive loads, to the torque transducer. Such telescoping ball spines are available from Sterling Instruments, as illustrated in the Handbook of Shafts, Bearings and Couplings, (1995) p. 4–9. The alternative embodiment of the apparatus 90 functions in the same manner described above with respect to apparatus 10.

The invention is further illustrated with reference to the following example.

EXAMPLE 1

The apparatus shown in FIGS. 1–5 is used for illustrative purposes in this example.

Both ends of an uncured polymer filament 34 are secured by the spring-loaded fiber securing clamps of the equal diameter windup drums 18, 20 of the extensional rheometer 10. A motor rotating at a fixed rotational rate drives the primary windup drum 18 and a fine toothed spur gear 36 on the same shaft 14. This spur gear 36 intermeshes with a similar spur gear 26 on the shaft 26a connected to the secondary windup drum 20.

Figure 9:
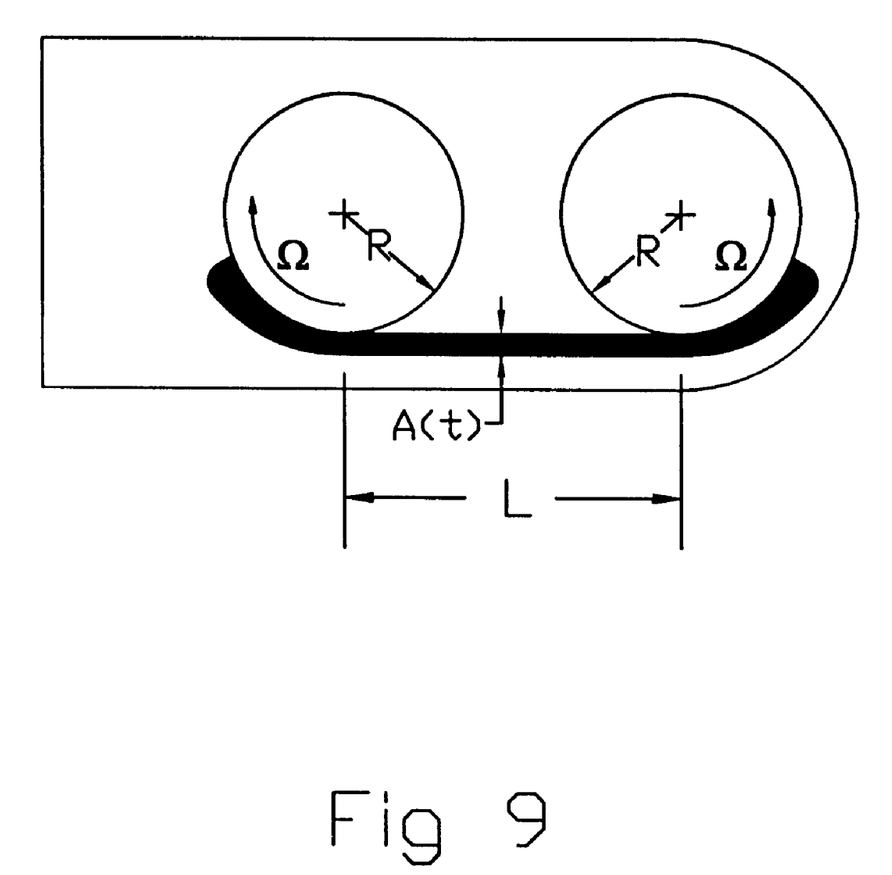
FIG. 9 is a graphic illustration of the top view of the primary and secondary drums as a sample is stretched.

Since both spur gears are similar, motion of the primary drum 18 drives an equal but opposite rotation of the secondary drum 20. The shafts of both drums are affixed with precision radial ball bearings 28 housed in the torque armature 16. The constant rotational speed ($\Omega$) of the drums of equal radius (R) imparts a constant, uniform extensional deformation rate ($\epsilon$) to the unsupported length (L) of the fiber 34 such that:

$$\epsilon = 2\Omega R/L$$

as illustrated graphically in FIG. 9.

The extension of the fiber offers a resistance to deformation due to the extensional viscosity $\eta_E$ (t) of the fiber, which in turn offers a resistance to the drum rotation in the form of torque $T_E$. The extensional viscosity of the fiber can be expressed in the following relationship:

$$\eta_E(t) = \sigma_E(t)/\epsilon = F_E(t)/A(t)/\epsilon$$

where $\sigma_E$ (t) is the instantaneous extensional stress in the unsupported fiber, $F_E$ (t) is the instantaneous force required to stretch the unsupported fiber, and A(t) is the instantaneous cross-sectional area of unsupported fiber. The resultant torque acting on the drums may then be expressed as:

$$T_E(t) = F_E(t)\, 2R$$

Both of these expressions may be combined to yield:

$$\eta_E(t) = T_E(t)/(2R\, \epsilon\, A(t))$$

By measuring the resultant torque on the armature, the extensional viscosity of the fiber may be calculated for a given extensional deformation rate and temperature.

$T_E$ can be resolved by a summation of torques about point 0 from FIG. 9. Thus, the resistance of the fiber to extend imparts a torque on the gear teeth which in turn imparts a resultant torque, $T_R$, on the torque armature. Since the bearings and intermeshing gears also offer resistance to rotation, a summation of torques yields:

$$\Sigma T_0 = 0 = T_R - T_E - T_{Gears} - T_{Bearings} = T_R - T_E - T_{Friction}$$

Thus, the above expression for $\eta_E$ (t) can be rewritten as:

$$\eta_E(t) = (T_R(t) - T_{Friction})/(2R\, \epsilon\, A(t))$$

where $T_R(t)$ is the resultant torque measured on the torque armature shaft by the torque transducer as a function of time, and $T_{Friction}$ is the torque losses from the bearings and gears which can be determined from calibration.

Now for a fiber in simple extension, A(t) can be expressed as:

$$A(t) = A_o \exp(-\epsilon t)$$

where $A_o$ is the original cross-sectional area prior to fiber extension. Substituting the initial expression for $\epsilon$, A(t) can be rewritten as:

$$A(t) = A_o \exp(-2\Omega R\, t)/L$$

Since $\Omega = d(\theta(t))/dt$ where $\theta(t)$ is the angular rotation of the primary windup drum as a function of time, then for a constant rotational drum speed, $\Omega$ may be expressed as:

$$\Omega = (\theta_2 - \theta_1)/(t_2 - t_1)$$

If it is assumed that $\theta_1 = 0$ at $t_1 = 0$ and that a constant rotational speed is achieved instantaneously then the expression for $\Omega$ simplifies to:

$$\Omega = \theta_2/t_2 = \theta(t)/t$$

Assuming no-slip of the fiber on the drum, the above expression can be substituted into the expression for A(t) and the following can be obtained:

$$A(t) = A_o \exp(-2\theta(t)R\, t)/(tL) = A_o \exp(-2\theta(t)\, R/L)$$

Thus, the resulting expression for the instantaneous cross-sectional area of the fiber sample is only a function of the angular rotation of the primary windup drum at a given time, t. Beyond the realm of validity of the aforementioned assumptions, however, more rigorous empirical methods for determining instantaneous fiber cross-sectional area should be applied and are well known to those skilled in the art.

Note that each windup drum can be threaded to allow for fiber alignment and multiple drum rotations to allow for very large Hencky strains. In doing so, however, the increased extensional deformation per drum revolution must be accounted for in the expression for extensional deformation rate, $\epsilon$. In addition, a non-circumferential force component must be accounted for in the torque measurement, $T_R(t)$.

While the invention has been specifically illustrated and described, those skilled in the art will recognize that the invention may be variously modified and practiced without departing from the concepts of the invention. The scope of the invention is limited only by the following claims.

What is claimed is:

1. An apparatus for measuring the extensional deformation rate of a sample, comprising:
   (a) a drive shaft attached to an armature wherein the armature is further connected to a torque shaft that does not move;
   (b) primary and secondary rotatable drums in proximity to one another, wherein said primary and secondary drums are mounted in said armature whereby said drive shaft rotates said primary and secondary drums in opposite directions of rotation; and
   (c) torque transducer means activated by the torque shaft for measuring the torque created on the torque shaft by said armature in response to the rotation of the primary and secondary drums.

2. The apparatus of claim 1 wherein said primary and secondary drums are in substantially parallel alignment, are mounted on bearings, and have associated therewith means for directing a windup of the sample on said primary and secondary drums.

3. The apparatus of claim 2 wherein the means for directing the windup of the sample is helical threading on each of said primary and secondary drums.

4. The apparatus of claim 1 wherein said primary and secondary drums are geared to be counter rotating.

5. The apparatus of claim 2 wherein the means for directing the windup of a sample is helical threading on each of said drums.

6. The apparatus of claim 3 wherein each of said primary and secondary drums is geared and said gears intermesh such that said drums rotate at the same speed.

7. The apparatus of claim 1 wherein each said primary and secondary drums has securing means for securing the sample thereto.

8. The apparatus of claim 1 wherein the armature is disposed in an environmental chamber.

9. A method for measuring the rate of flow of low modulus solids comprising the steps of
   (a) providing an apparatus for measuring the rate of extensional flow of low modulus solids comprising, a drive shaft mounted in an armature wherein the armature is further connected to a torque shaft, and mounted in the armature are two rotatable drums in proximity to one another, wherein a first said drum is mounted in said armature substantially in alignment with said torque and drive shafts, and a second said drum is adjacent thereto
   (b) fixing a sample to both said drums, one end of said sample being attached to each said drum
   (c) causing the two ends of the sample to be pulled away from each other by rotation of the drums, and
   (d) measuring the torque created in the torque shaft by the drawing of the sample.

10. The method of claim 9 which comprises the further steps of
    (a) measuring the maximum torque achieved by the sample, and
    (b) measuring the time elapsed from the start of the measurement to breaking of the sample.

11. The method of claim 9 which comprises the further steps of disposing said first and second drums in substantially parallel alignment, mounting said drums on bearings, and associating therewith means for directing the windup of a sample on said drums.

12. The method of claim 9 which comprises the further step of gearing said drums to be counter rotating.

13. The method of claim 9 which comprises the further step of providing each said drum with gearing and causing said gears to intermesh such that said first and second drums rotate at the same speed.

14. The method of claim 9 which comprises the further step of providing each said drum with securing means for securing a sample thereto.

15. A method for measuring the measuring the extensional deformation rate of a sample comprising the steps of
    (a) providing an apparatus for measuring the extensional deformation rate of a sample comprising, a drive shaft mounted to an armature wherein the armature is further connected to a torque shaft, and mounted in the armature are a primary rotatable drum and a secondary rotatable drum, said primary and secondary rotatabale drums being in proximity to one another, wherein the primary drum is mounted to said armature substantially in alignment with said drive shaft;
    (b) fixing the sample to said primary and secondary drums, one end of said sample being attached to said primary drum and another end of said sample being attached to said secondary drum;
    (c) causing the ends of the sample to be pulled away from each other by rotation of the primary and secondary drums, and
    (d) measuring the torque created in the torque shaft by the ends of the sample being pulled away from each other by windup of the sample on the drums.

16. The method of claim 15 which comprises the further steps of
    (a) measuring the maximum torque achieved by the sample, and
    (b) measuring the time elapsed from the start of the measurement to breaking of the sample.

17. The method of claim 15 which comprises the further steps of disposing said primary and secondary drums in substantially parallel alignment, mounting said drums on bearings, and associating therewith means for directing the windup of the sample on said drums.

18. The method of claim 15 which comprises the further step of gearing said drums to be counter rotating.

19. The method of claim 15 which comprises the further step of providing each of said drums with gearing and causing said gears to intermesh such that said primary and secondary drums rotate at the same speed.

20. The method of claim 15 which comprises the further step of providing said primary and secondary drums with securing means for securing a sample thereto.

* * * * *